United States Patent [19]
Leise, Jr. et al.

[11] Patent Number: 6,093,276
[45] Date of Patent: Jul. 25, 2000

[54] IN-LINE METHOD OF MANUFACTURE OF OSTOMY APPLIANCE FACEPLATE

[75] Inventors: Walter F. Leise, Jr., Lindenhurst; Ronald S. Botten, Gurnee; John W. McDonald, Jr., Lake Zurich; Demetrios Rigas, Northbrook, all of Ill.; James J. Passalaqua, Paddock Lake, Wis.

[73] Assignee: Hollister Incorporated, Libertyville, Ill.

[21] Appl. No.: 09/095,991

[22] Filed: Jun. 11, 1998

[51] Int. Cl.[7] .......................... B32B 31/06; B32B 31/08; B32B 31/12; B32B 31/18
[52] U.S. Cl. .......................... 156/249; 156/242; 156/269; 156/297; 156/324; 604/338
[58] Field of Search .................................... 156/249, 242, 156/269, 297, 324; 604/338

[56] References Cited

U.S. PATENT DOCUMENTS

| | | |
|---|---|---|
| 4,419,174 | 12/1983 | Jensen . |
| 4,685,990 | 8/1987 | Ferguson . |
| 4,753,703 | 6/1988 | Jensen ................................. 156/269 X |
| 4,775,374 | 10/1988 | Cilento et al. .......................... 604/344 |
| 5,185,008 | 2/1993 | Lavender ................................ 604/338 |
| 5,316,607 | 5/1994 | Johnsen et al. . |
| 5,716,475 | 2/1998 | Botten et al. ........................... 156/219 |
| 5,730,735 | 3/1998 | Holmberg et al. . |
| 5,935,363 | 8/1999 | Gilman et al. ...................... 156/269 X |

Primary Examiner—Curtis Mayes
Attorney, Agent, or Firm—Tilton Fallon Lungmus

[57] ABSTRACT

A low-profile faceplate assembly for a two-piece ostomy appliance, and a method for manufacturing it, are disclosed. The faceplate includes a wafer of an adhesive skin barrier material and a flexible plastic coupling ring (for detachably coupling the faceplate to an ostomy pouch having a mating ring), and is distinguished by the mounting flange of the coupling ring being embedded within the faceplate. The faceplate is made by a convergence of in-line processes taking place simultaneously with an injection/compression molding operation for the skin barrier wafer as disclosed in U.S. Pat. No. 5,716,475, thereby eliminating or greatly reducing the assembly labor for the various process steps plus the handling, storing and transferring steps commonly associated with the manufacture of ostomy faceplate assemblies.

12 Claims, 3 Drawing Sheets

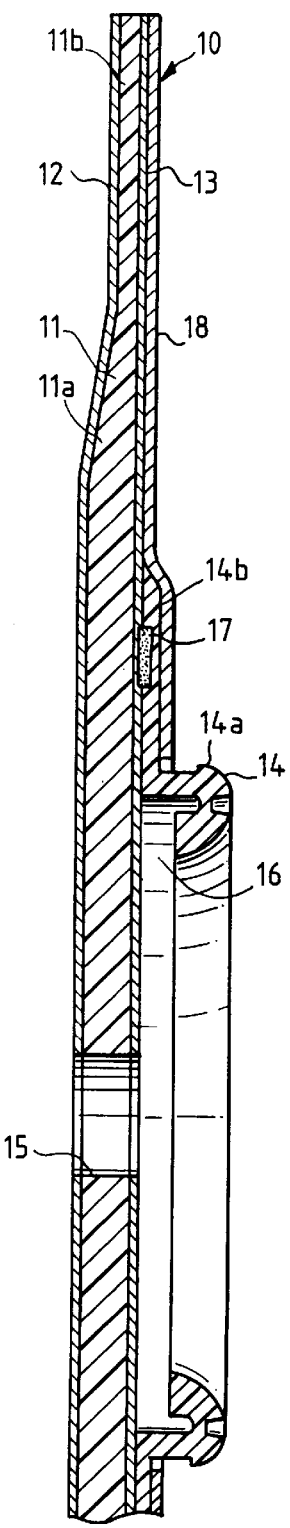
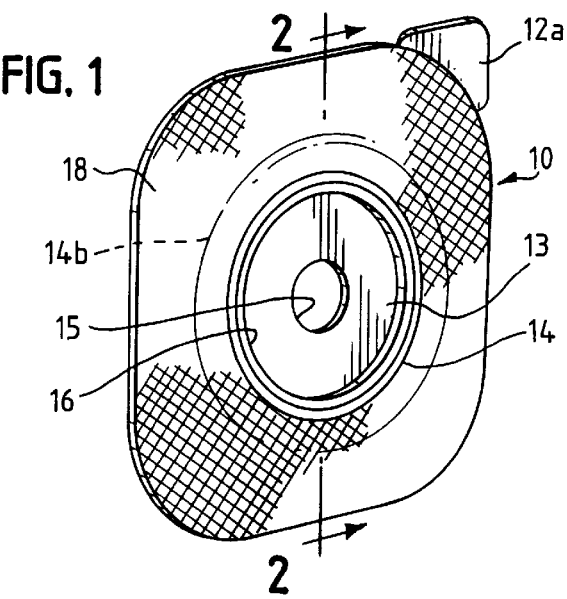
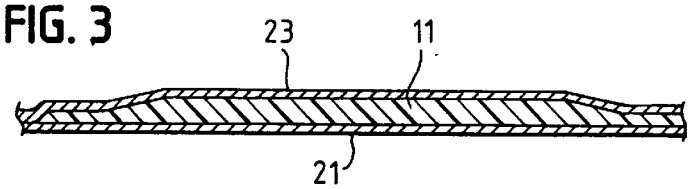
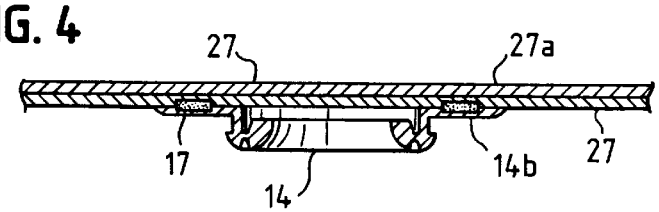
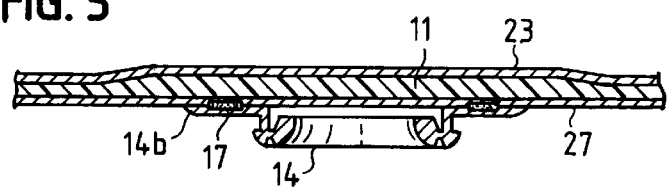
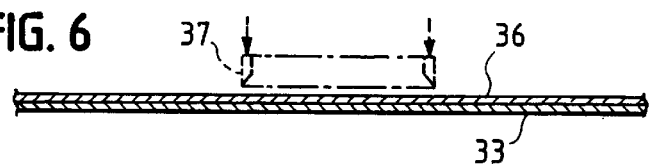
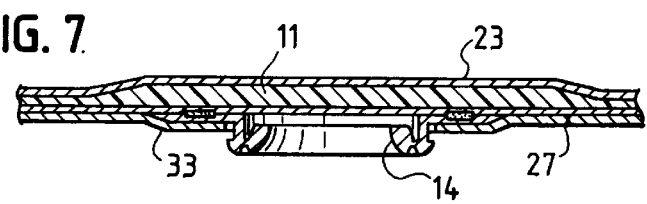

IN-LINE METHOD OF MANUFACTURE OF OSTOMY APPLIANCE FACEPLATE

BACKGROUND OF THE SUMMARY

In conventional manufacture of the faceplate assemblies for use with two-piece ostomy appliances, it is common practice to produce and store each of the several components and then join them together, often by hand, at the time of final assembly. For example, adhesive wafers are customarily manufactured by extruding skin barrier material onto a receiving web and then die-cutting and storing the wafers for later assembly with other parts or sub-assemblies needed for the final product. While it might be thought that manufacturing efficiencies are enhanced by high-speed production of each of the various components and sub-assemblies, just the opposite is believed to be the case if subsequent assembly steps occur at different locations, or at different times, and require storage, handling, and additional procedures such as inspections or re-inspections, further testing, and the like. Furthermore, high-speed production equipment often has the disadvantage of being difficult and time-consuming to convert to the manufacture of similar components differing in size, shape or composition—compelling reasons for favoring large production runs which in turn increases the problems of handling and storage operations.

Co-owned U.S. Pat. No. 5,716,475 is directed to a method of making wafers of adhesive skin barrier material that does not involve extruding a sheet or web of such material and then die-cutting the sheet to form the individual wafers. Instead, such wafers are formed by an injection and compression molding operation in which discrete mounds of soft, pliant barrier material are deposited one-by-one on an intermittently-advanced web, covered by a second web, and then compressed into the desired shape. Although not as adaptable as extrusion techniques for high-speed production of wafers, the patented method results in products that are considered superior in quality because the molecular orientations of each wafer are more uniform in radial directions in contrast to wafers of extruded barrier material which tend to have molecular orientations predominately in the machine direction and, as a result, have physical properties that can be considerably different depending on the direction of measurement.

One aspect of this invention lies in the discovery that the injection/compression molding method of the aforementioned patent has the further advantage of being particularly amenable to coordination with automated production of other components, with all such operations being carried out simultaneously and continuously in an in-line fashion to yield finished products, thereby eliminating most if not all of the problems and expenses of handling, storage and transfer described above. More specifically, the method of the present invention is a combination of in-line operations in which the assembling procedures are integrated with the molding, forming, cutting, and other parts-making operations to provide a continuity of automated steps resulting in the production of finished products, thereby greatly reducing the labor content in the manufacturing cost.

A still further aspect of the invention involves the discovery that the in-line procedures of this invention differ from prior manufacturing procedures in being particularly suitable for the fabrication of ostomy faceplates of superior construction, function and appearance. A faceplate embodying this invention comprises a coupling ring having a radially outwardly-extending flange portion that is embedded within the faceplate and is therefore not visible or subject to exposure from either side of the faceplate. In addition to appearance advantages, such a construction shields the flange portion of the coupling ring, prevents liquids (and solids) from migrating inwardly between the outer edge of the flange portion and the front (pouchside) surface of the faceplate, and enhances the security of attachment between the coupling ring and the faceplate per se. A protective cover layer is preferably formed of a soft, flexible nonwoven fabric and extends without interruption from the annular connecting portion of the coupling ring to the outermost limits of the faceplate. Unlike many other faceplate constructions that also utilize nonwoven fabric, usually in the form of windowframing strips or rings of microporous adhesive tape, the faceplate of this invention utilizes hydrocolloid-containing skin barrier material as a skin-friendly moisture-absorbing adhesive and as the sole means for securing the entire bodyside surface of the faceplate to the peristomal skin surfaces of a wearer. A liquid-impervious backing film interposed between the layer of skin barrier adhesive and the nonwoven layer, and coextensive in area with the liquid-absorbing adhesive layer, prevents strike-through of effluent into the nonwoven fabric. Thus, the backing film, skin barrier adhesive layer, and nonwoven layer all have coextensive outer peripheral edges.

Other features, advantages, and objects of the invention will become apparent from the specification and figures.

DRAWINGS

FIG. 1 is a perspective view of an ostomy faceplate embodying this invention.

FIG. 2 is an enlarged cross sectional view taken along line 2—2 of FIG. 1.

FIGS. 3–7 are fragmentary sectional views taken in the direction of web movement and illustrating the condition of various components and their assemblies at different stages in the manufacturing process depicted in FIG. 8.

DETAILED DESCRIPTION OF PREFERRED EMBODIMENTS

Figure 8:
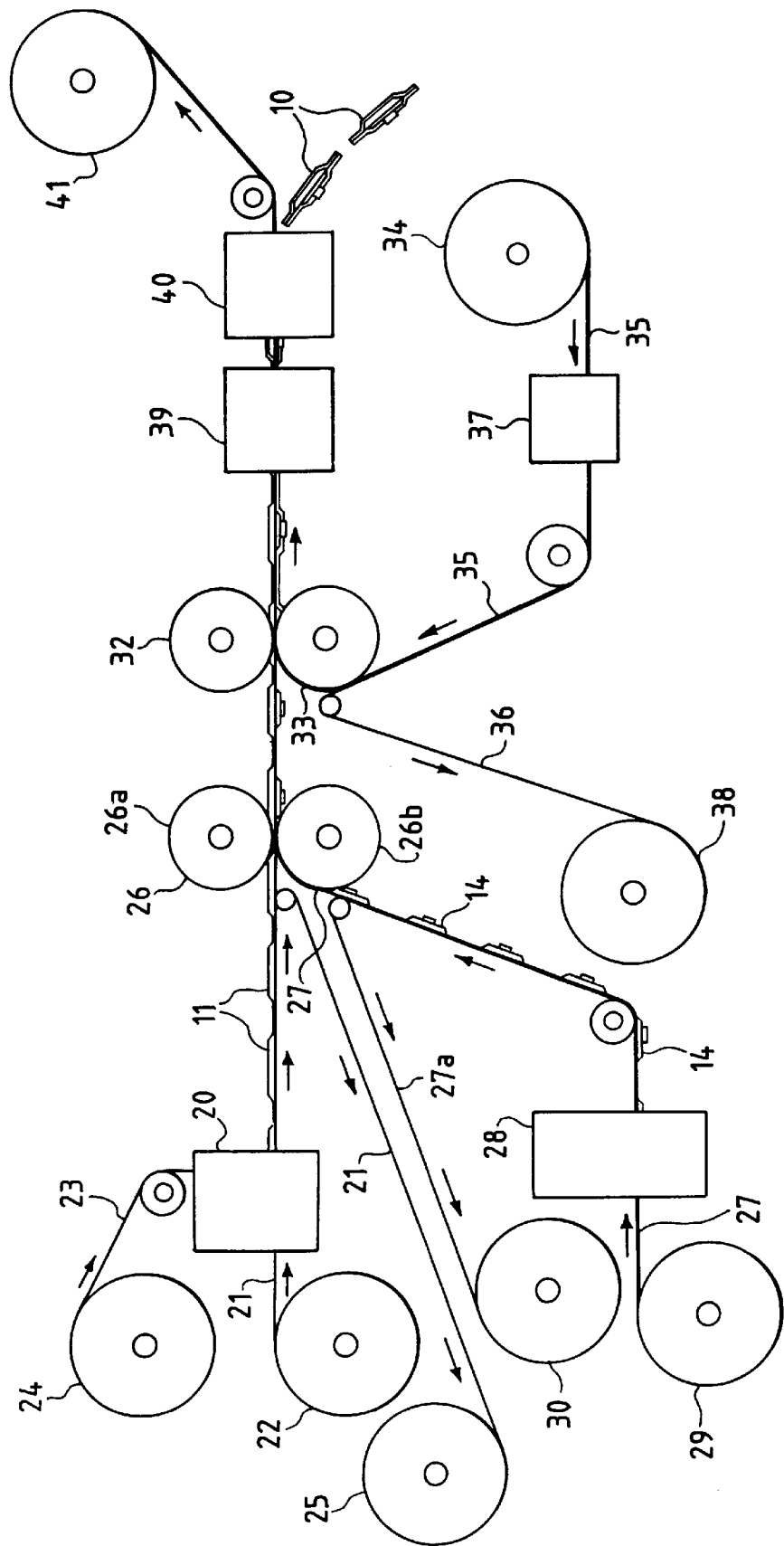
FIG. 8 is a schematic view illustrating the simultaneous procedures of the manufacturing process of this invention.

Referring to FIGS. 1 and 2, the numeral 10 generally designates a faceplate for a two-piece ostomy appliance. The faceplate as shown is generally rectangular (square) in outline with rounded corners, but other shapes, such as circular or oval shapes, may be provided. The faceplate includes a wafer or layer 11 of moisture-absorbing adhesive skin barrier material having a bodyside surface covered by a removable release sheet 12, an opposite surface covered by a thin backing film 13, and a coupling ring 14 secured to film 13.

The term "skin barrier" is widely used in the medical field, and is used herein, to refer to any of a variety of materials in which a soft, sticky, and pliant adhesive composition constitutes a continuous phase and particles of one or more liquid-absorbing and swellable hydrocolloids are dispersed throughout the adhesive and constitute a discontinuous phase. The adhesive phase contains at least one elastomer such as polyisobutylene, often in combination with one or more tackifiers, plasticizers, and antioxidants. An elastomer such as a styrene-isoprenestyrene block copolymer (e.g., "Cariflex" TR-1107, from Shell Chemical Co.) or a styrene- butadiene-styrene block copolymer (e.g., "Kraton" 1100 Series, from Shell Chemical Co.) may be included, and other ABA block copolymers, such as ethylene-propylene block copolymers known as EPR rubbers have also been included in adhesive compositions for increasing the elastomeric properties of such barrier materials.

The discontinuous phase may be particles of any suitable hydrocolloid or mixtures of hydrocolloids such as sodium carboxymethylcellulose, calcium carboxymethyl-cellulose, pectin, gelatin, and natural gums such as guar gum, gum arabic, locust bean gum, karaya, and the like. Such hydrocolloids are water-absorbing and water-swellable. They absorb moisture from the skin and contribute to the wet tack characteristics of the skin barrier material, all as well known in the art.

As shown in FIG. 2, the skin barrier wafer 11 may be contoured, having a relatively thick central body portion 11a and a thinner peripheral flange portion 11b. The thickness of the body portion increases the moisture absorbing capacity of the wafer and promotes an effective seal directly about a patient's stoma, whereas the thinness of the peripheral portion enhances flexibility and compliance with the skin and reduces the possibility that channeling and leakage might occur. While such contouring is therefore considered highly advantageous, it is nevertheless optional and, if desired, the wafer 11 may instead be of the same uniform thickness throughout its full extent.

Release sheet 12 is formed of any suitable material that is tough, flexible, and substantially non-stretchable. Siliconized paper may be used effectively. A polymeric material, such as polyethylene terephthalate, is particularly desirable because of its high tensile strength and transparency, but other thermoplastic materials having similar properties may be used. An anti-stick coating of silicone may be provided on the release sheet and, as shown in FIG. 1, a tab portion 12a of the release sheet projects beyond barrier layer 11 to facilitate removal when the faceplate is to be adhered to the skin.

Backing film 13 is composed of a flexible elastomeric material such as polyurethane. Other polymeric materials having similar properties are well known in the art and may be used. The wafer 11, along with backing film 13 and release sheet 12, are provided with a central opening 15 which, in the embodiment illustrated, serves as a starter opening to be enlarged (by cutting with scissors) to match the shape and size of a patient's stoma. Alternatively, opening 15 may be pre-sized to eliminate the need for cutting at the time of application. If desired, the opening may be formed during manufacture to match the inside diameter of coupling ring 14.

Coupling ring 14 is formed of low-density polyethylene or other flexible thermoplastic material having similar properties and has an annular connecting portion 14a defining a stoma-receiving opening 16 and a radially outwardly extending flange portion 14b for attachment to backing film 13. The particular coupling ring illustrated in the drawings is similar to one shown and described in co-owned U.S. Pat. No. 5,185,008, the disclosure of which is incorporated by reference herein. It is to be understood, however, that details of connecting portion 14a are not critical to the present invention and that a ring having a connecting portion of somewhat different construction and operation may be provided. What is significant is that the annular connecting portion 14a must extend axially away from the planar flange portion 14b, that it defines a stoma-receiving opening 16, and that it is adapted for mechanically coupling to a second ring provided by an ostomy pouch (not shown).

Flange 14b is securely affixed by annular heat seal 17 to backing film 13. Ideally, only a single heat seal is provided and, as shown in FIG. 2, is spaced radially inwardly from the outer periphery of flange 14b.

A flexible cover layer 18 extends over the front surface of flange 14b and the surface of film 13 located radially outwardly beyond the flange. Therefore, as shown most clearly in FIG. 2, the annular flange is embedded or sandwiched between cover layer 18 and film 13. The advantages are partly aesthetic since such construction enhances the low-profile appearance of the faceplate assembly and provides an unbroken surface extending from connecting portion 14a of the coupling ring all the way to the outer periphery of the faceplate. However, the construction also has important functional advantages since it protects the edge portions of flexible flange 14b from pulling away from film 13 (or vice versa), prevents liquids or particulates from entering the space between the periphery of the flange and the film, and enhances the security of attachment between the flange and the backing film of the wafer.

Cover layer 18 may be formed of any of a variety of flexible and stretchable materials. Most advantageously, however, it is composed of a soft, flexible and stretchable fabric, particularly a nonwoven fabric such as a spunbonded low density polyethylene fabric available under the designation "Daltex" 6080-A1-UPE from Don & Low Ltd., Forfar, Scotland. Other materials having somewhat similar properties that might be used include flexible and resilient polymeric foam materials of either open or closed cell structure. A pressure-sensitive adhesive coating upon the bodyside surface of cover layer 18 secures that layer to both the flange 14b and the surface of the backing film surrounding the flange. The cover layer 18, backing film 13, and adhesive layer 11 all have the same outermost limits with the skin barrier adhesive layer constituting the sole means for adhering the faceplate to the peristomal skin surfaces of a patient.

FIG. 8 schematically depicts a continuous in-line process for making faceplates 10. Numeral 20 designates an injection/compression molding apparatus as shown and described in co-owned U.S. Pat. No. 5,716,475, the disclosure of which is incorporated herein by reference. The apparatus includes upper and lower platens that intermittently separate and close as a web 21 from supply roll 22 is indexed forwardly. Each time the platens separate, a discrete mound of heated skin barrier material is deposited onto web 21. A second web 23 of flexible and substantially non-stretchable material from supply roll 24 is positioned over the mound and, as the platens close together during the compression step, each mound is formed into a wafer of predetermined size and shape. This results in a series of discrete, spaced-apart wafers 11 of skin barrier material sandwiched between the first and second webs 21 and 23 and carried by such webs out of the injection/compression molding station 20 in which they were formed (FIG. 3).

The upper or second web 23 is used to make the release sheets 12 of faceplates 10 and is preferably composed of a material such as polyethylene terephthalate as previously described. Lower or first web 21 may be sacrificial (as shown) or non-sacrificial. As a sacrificial element, web 21 may be formed of siliconized paper or a non-stretchable polymeric material that is coated or treated so that it may be peeled away from the wafer and rewound into roll 25. Alternatively, web 21 may take the form of a continuous belt having a non-stick support surface that travels through the injection/compression molding station 20 and extends to the delaminating/laminating station 26.

At the time that wafers are being formed at the injection/compression molding station 20, coupling rings are being affixed to a third web 27 at attachment station 28. Web 27 is supplied from roll 29 and is ultimately used as the flexible backing film 13 for the faceplates, already described as being stretchable as well as thin and flexible. To facilitate processing and subsequent assembly operations, web 27 is supplied with its back surface coated with a suitable pressure-sensitive adhesive and covered with a removable reinforcing layer 27a of siliconized paper or other flexible but substantially non-stretchable material. As the coupling rings carried by web 27 approach station 26, paper layer 27a is peeled away and rewound upon roll 30.

Coupling rings 14 are attached to web 27 by annular heat seals 17 between the flanges of the coupling rings and the film of the web as shown in FIG. 4. Station 28 may therefore consist only of a heat sealing station in which preformed coupling rings are successively attached to web 27. However, if desired, station 28 might additionally include molding operations in which the coupling rings are formed as well as subsequently attached to the web.

The wafers 11 carried by webs 21 and 23 and the coupling rings carried by web 27 converge in synchronized fashion at the delamination/lamination station 26. At that point, the elements appear as schematically depicted in FIGS. 3 and 4. Before entering the nip between laminating rollers 26a and 26b, the first web 21 is stripped from the undersides of wafers 11 and sacrificial reinforcing layer 27a is stripped from the third web 27. The third web 27 is brought into contact with the second web 23 and the undersurfaces of the molded wafers 11 carried thereby, resulting in the combination illustrated in FIG. 5. As the laminate leaves station 26, web 27 remains adhered to the undersides of wafers 11 because of the adhesiveness of the skin barrier material as well as any adhesive coating carried by the web 27 itself, such coating also serving the purpose of holding webs 23 and 27 together in areas surrounding each of the discrete wafers of the series.

The next station of the in-line process is laminating station 32 where a fourth web 33 of flexible covering material is applied to the third web 27 and to the flanges 14b of the coupling rings heat sealed to web 27. Web 33 is preferably formed of nonwoven fabric and will become the covering layer 18 of the finished faceplates. Since such nonwoven material is too soft and deformable to be processed in such an in-line operation without reinforcement, the web is provided by supply roll 34 in the form of a laminate 35 in which the nonwoven layer is temporarily secured by a pressure-sensitive coating to a non-stretchable reinforcing release layer 36. The composite web 35 first passes through a punching station 37 where openings slightly larger than the connecting portions 14a of coupling rings 14 are die-cut into the composite web (see FIG. 6). The web then travels to station 32 where the reinforcing backing 36 is stripped away and rewound on roll 38, and the nonwoven covering layer is adhesively secured to the surfaces of flanges 14b and web 27. The combined webs, in the condition illustrated in FIG. 7, with the coupling rings 14 heat sealed in place and their flanges sandwiched between webs 33 and 27, then advance to cutting stations 39 and 40. At station 39, the central openings 15 are cut through the wafers and the webs in contact with them, and at station 40 the final cutting of the outer periphery of each faceplate takes place. The faceplates 10 are discharged as finished products from station 40, and the web materials previously around such faceplates are carried as waste material to a scrap rewind role 41.

Figure 9:
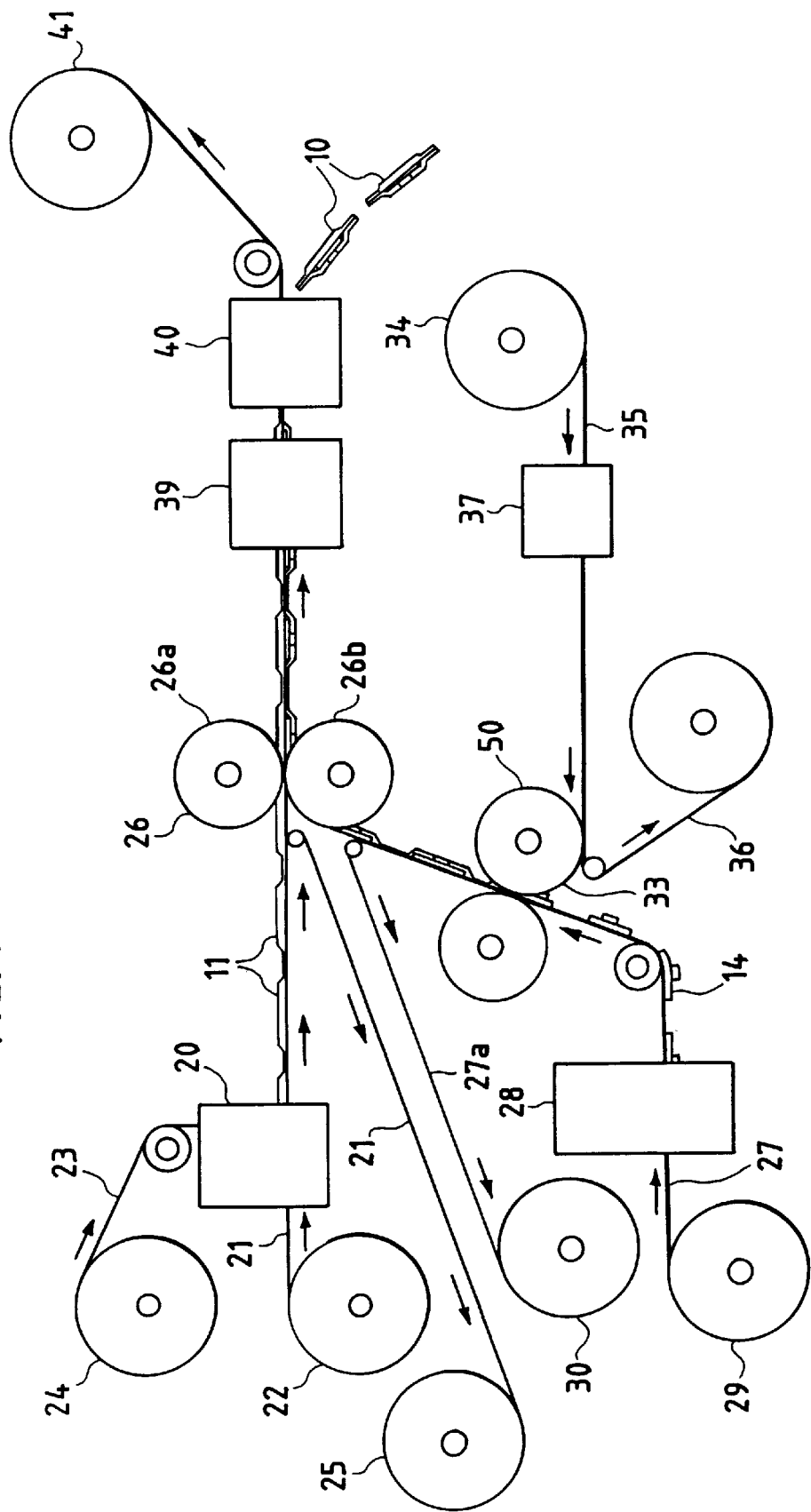
FIG. 9 is a schematic view illustrating a second embodiment of the manufacturing process of the invention.

The embodiment of FIG. 9 is similar to that of FIG. 8 except that the order of the two delamination/lamination stations is reversed. In the process of FIG. 8, the fabric fourth web 33 is laminated to the other webs after the film of the third web 27 has been applied to the wafers 11 carried by second web 23. In FIG. 9, the fabric web 33 is joined to web 27, and to the flanges of the coupling rings 14 heat sealed to that web before the two webs reach the delamination/lamination station 26. Thus, the fourth web that ultimately constitutes the covering layer of each wafer is applied at laminating/delaminating station 50, causing the nonwoven covering layer to be applied to the combination depicted in FIG. 4 in advance of the convergence of the combinations of FIGS. 3 and 4 at delamination/lamination station 26.

While in the foregoing we have disclosed embodiments of the invention in considerable detail, it will be understood by those skilled in the art that many of these details may be varied without departing from the spirit and scope of the invention.

What is claimed:

1. An in-line method of making adhesive faceplates for two-piece ostomy appliances comprising the steps of intermittently advancing flexible first and second webs through an injection/compression molding station in which discrete mounds of soft, adhesive skin barrier material are deposited on one of said webs and are then successively compressed between said webs to form a series of wafers of skin barrier material of selected size and shape; simultaneously affixing a series of thermoplastic coupling rings with annular attachment flanges to one side of a flexible third web, with said coupling rings being affixed to said third web by said attachment flanges, and advancing said third web with said coupling rings carried thereby, and said first and second webs with said wafers therebetween, to a delaminating/laminating station; stripping said first web and replacing the same with said third web in synchronized relation at said delaminating/laminating station with each of said coupling rings being directly aligned with each of said wafers; providing a cover-applying station and laminating at said cover-applying station a fourth web of flexible covering material to both said third web and said flanges of said coupling rings; said fourth web having a series of uniformly-spaced openings therein with each opening being sized and located to register with one of said coupling rings at said cover-applying station to expose a portion of each coupling ring therethrough while at the same time covering the annular attachment flanges thereof, thereby sealing said attachment flanges of said series of coupling rings between said third and fourth webs; and thereafter advancing said second, third and fourth webs with said wafers and coupling rings carried thereby to a cutting station where said second, third and fourth webs are cut at or just within the periphery of each wafer, thereby detaching a succession of discrete adhesive faceplates from said webs.

2. The method of claim 1 in which said step of laminating said fourth web of flexible covering material to both said third web and said coupling rings at said cover-applying station occurs beyond said delaminating/laminating station.

3. The method of claim 1 in which said step of laminating a fourth web of flexible covering material to both said third web and said coupling rings at said cover-applying station occurs in advance of said delaminating/laminating station.

4. The method of claim 1 in which said fourth web is adhesive-coated on one side and said adhesive coating is brought into contact with said third web and said flanges of said coupling rings at said cover-applying station.

5. The method of claim or 2 in which a flexible but substantially non-stretchable backing covers the adhesive coating of said fourth web and is stripped from said fourth web to expose said adhesive coating to said flanges and said third web at said cover-applying station.

6. The method of claim 1 in which said fourth web is formed of fabric.

7. The method of claim 6 in which said fabric of said fourth web is nonwoven.

8. The method of claim 1 in which there is the further step of cutting said second and third webs and said wafers at said cutting station to form an opening therethrough located at the center of each coupling ring.

9. The method of claim 1 in which there is the further step of contouring each of said wafers at said injection/compression molding station, with each wafer being contoured to provide a thin peripheral portion and a thicker central body portion.

10. The method of claim 1 in which said third web is formed of heat-sealable thermoplastic material and said step of affixing said coupling rings to said third web occurs by heat sealing said flanges of said coupling rings to said third web in advance of said delaminating/laminating station.

11. The method of claim 10 in which said third web has a flexible but substantially non-stretchable backing laminated thereto; said backing being stripped from said third web before said third web is laminated to said wafers and said second web at said delaminating/laminating station.

12. The method of claim 10, in which said third web is adhesive-coated and the adhesive coating thereof is brought into contact with said wafers and said second web at said delaminating/laminating station.

* * * * *